(12) United States Patent
Long et al.

(10) Patent No.: US 7,261,728 B2
(45) Date of Patent: Aug. 28, 2007

(54) BIOPSY FORCEPS DEVICE AND METHOD

(75) Inventors: Gary L. Long, Mariemont, OH (US);
David Stefanchik, Mason, OH (US);
James A. Craft, Lexington, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 437 days.

(21) Appl. No.: 10/099,086

(22) Filed: Mar. 15, 2002

(65) Prior Publication Data
US 2003/0176880 A1 Sep. 18, 2003

(51) Int. Cl.
*A61B 10/06* (2006.01)
*A61B 17/29* (2006.01)

(52) U.S. Cl. .............. 606/207; 606/170; 600/104; 600/153

(58) Field of Classification Search ........... 606/110, 606/115, 170, 174, 205, 208; 600/107
See application file for complete search history.

(56) References Cited

U.S. PATENT DOCUMENTS

| | | | |
|---|---|---|---|
| 3,915,157 A | 10/1975 | Mitsui | |
| 4,741,326 A | 5/1988 | Sidall et al. | |
| 4,763,662 A * | 8/1988 | Yokoi | 600/101 |
| 4,949,706 A | 8/1990 | Thon | |
| 5,037,433 A | 8/1991 | Wilk et al. | |
| 5,106,369 A | 4/1992 | Christmas | |
| 5,109,830 A | 5/1992 | Cho | |
| 5,217,460 A * | 6/1993 | Knoepfler | 606/205 |
| 5,217,479 A * | 6/1993 | Shuler | 606/180 |
| 5,273,026 A | 12/1993 | Wilk | |
| 5,386,818 A | 2/1995 | Schneebaum et al. | |
| 5,954,731 A * | 9/1999 | Yoon | 606/144 |
| 6,106,521 A | 8/2000 | Blewett et al. | |
| 6,352,503 B1 | 3/2002 | Matsui et al. | |
| 6,458,074 B1 * | 10/2002 | Matsui et al. | 600/106 |
| 6,551,315 B2 * | 4/2003 | Kortenbach et al. | 606/207 |

\* cited by examiner

*Primary Examiner*—Glenn K. Dawson

(57) ABSTRACT

An apparatus and method for providing a biopsy device at the distal end of a medical device, such as an endoscope, are disclosed. The apparatus can include a device attached to an endoscope to guide the position of the end of the instrument, such as by constraining the instrument to bend in a predetermined manner, or otherwise guide the distal end of the instrument extending from the distal end of the instrument channel.

1 Claim, 13 Drawing Sheets

BIOPSY FORCEPS DEVICE AND METHOD

This application is related to the following copending, concurrently filed patent applications: application Ser. No. 10/099,772 "Method for Controlling Position of Medical Instruments"; and application Ser. No. 10/098,250 "An Apparatus for use in Guiding an Instrument Used with an Endoscope" which are hearby incorporated herein by reference.

FIELD OF THE INVENTION

The present invention relates to medical instruments, in general, and, more particularly, to a medical device that can be used to perform a biopsy procedure using flexible instruments inserted in an endoscope.

BACKGROUND OF THE INVENTION

Physicians have often used endoscopes to examine, to biopsy, and to ablate the tissue of patients within lumens such as the esophageous and the bowel. These procedures include esophageal duodenoscopy, (EGD), colonoscopy, and polypectomy. Endoscopes used in these procedures can be several feet long and generally comprise one or more instrument channels and optical fiber bundles. The instrument channels and optical fiber bundles open into the body at the distal end of the endoscope and are generally parallel to the axis of the flexible endoscope. Physicians place flexible instruments through the instrument channels while visualizing and illuminating a site using the optical fiber bundles. The instruments have end-effectors at the distal end for performing useful therapeutic work to tissue. The instruments also provide at their proximal ends operating mechanisms for actuating the end-effectors. Such instruments placed through an instrument channel of an endoscope may include biopsy forceps for tissue sampling, electrical wires for radiofrequency ablation, or tubes used for irrigation, gas transfer, particular matter transfer, and suction.

A physician performing a therapeutic procedure with the use of an endoscope places a long, flexible instrument through the endoscope's instrument channel and then positions the instrument near the site within the body lumen where a therapeutic procedure is to be performed. The physician grasps the endoscope with one hand and introduces the flexible instrument from an entrance at the proximal end of the endoscope with the other. An assistant usually holds the proximal end of the flexible instrument and operates the mechanism at the proximal end of the instrument to actuate the end-effector.

Locating the end-effector within the lumen presents difficulties to the physician. The flexible instrument emerges from the instrument channel of the endoscope in a direction parallel to the axis of the endoscope. Many times work needs to be performed by the instrument at the inner wall of a body lumen, and at an angle to the axis of the endoscope. Much tedious maneuvering of both endoscope and instrument is needed to place the end-effector into a position to perform useful work. The flexible nature of the instrument creates difficulties in locating the end-effector at the needed position on the inner wall of the body lumen. Rotating the endoscope to accommodate the instrument causes the image on the monitor to rotate creating visualization difficulties for the physician.

When the task to be performed is a biopsy, a tissue sample or specimen must be transported away from the work site for collection. To collect the specimen, the physician pulls the entire instrument from the endoscope, removes the specimen, places the specimen into a collection jar, and replaces the instrument into the endoscope. The physician must then manipulate the instrument into a new position to take another specimen.

SUMMARY OF THE INVENTION

Applicants have recognized the need for apparatus for facilitating manipulation of surgical instruments at the distal end of an endoscope. The apparatus can comprise a device, such as a mechanism, associated with the distal end of an endoscope. The mechanism guides the position of a flexible instrument extending through or alongside the endoscope. In one embodiment, the mechanism can provide bending of a flexible instrument, while restricting twisting or other undesirable bending of the flexible instrument. In one embodiment, the mechanism can be used to provide cooperative motion between multiple flexible instruments.

The mechanism can comprise a pivot arm associated with a base, the pivot arm and base together forming an end cap that is releasably joined to the distal end of an endoscope. The pivot arm can engage a distal end of the instrument to constrain motion of the instrument, while permitting rotation of the distal end of the instrument. The pivot arm can provide curvature of the instrument, such as by bending, through an angle of at least about 90 degrees, and in one embodiment through at least about 180 degrees, while restricting twisting or other undesirable bending of the instrument. The pivot arm can be used to position the end of the instrument for performing work on tissue distal to and on the periphery of the endoscope. The pivot arm can also be used with the endoscope to perform multiple biopsies without withdrawing the endoscope from the patient's body. In one embodiment, the pivot arm can be used to provide cooperative motion of a first flexible instrument extending through the endoscope and a second instrument that is insertable alongside the endoscope or within a second channel of the endoscope.

One or more flexible instruments may include an end-effector with a sharp edge to cut tissue. One or more flexible instruments may include a hollow member to allow fluid, particulate, or gas to pass so that suction may be applied at the proximal end to retrieve tissue samples, or for providing a gas flow at a treatment site.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2A is a cross-section view taken through 2A-2A, showing a double-D hole and a counterbore in a pivot-arm base.

DETAILED DESCRIPTION OF THE INVENTION

Figure 1:
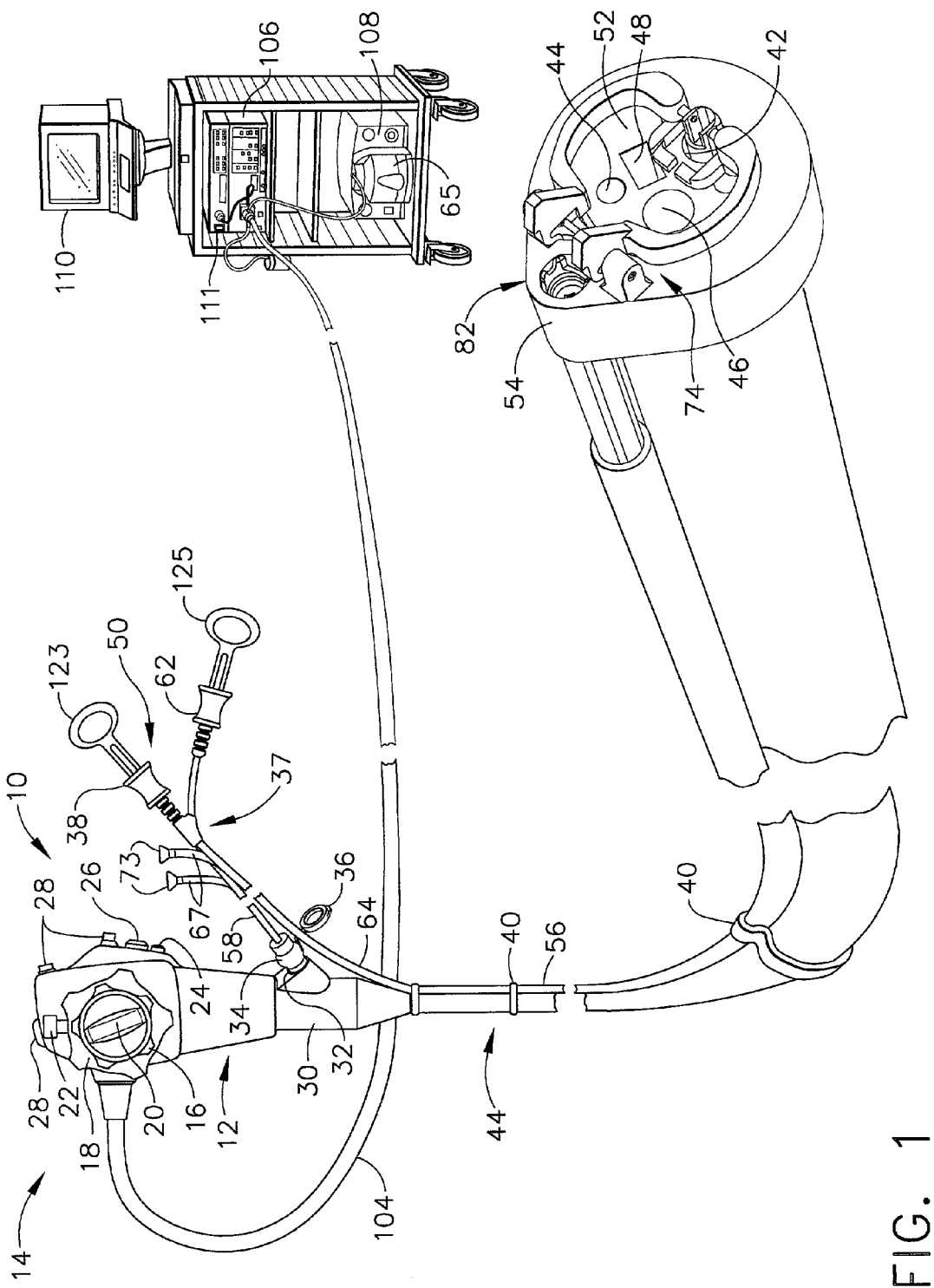
FIG. 1 is a view showing an end cap and biopsy forceps device according to an embodiment of the present invention assembled to an endoscope having associated videoscopic and pneumatic equipment.

FIG. 1 depicts a suitable version of an endoscope 14 in combination with one embodiment of the present invention. A suitable version of endoscope 14 can be the Olympus GIF-P140, and may be purchased from Olympus America, Inc., in Melville, N.Y.

A control section 10 is located at the proximal end of endoscope 14. A grip section 12 is on control section 10 for grasping of endoscope 14. Control section 10 also possesses a right/left angulation control knob 16 and an up/down angulation control knob 18 for angulating the distal end of endoscope 14. A right/left angulation lock 20 and an up/down angulation lock 22 are provided to lock their respective knobs into position. Endoscope 14 may further provide an air/water valve 24 and a suction valve 26 attached to control section 10. Remote switches 28 extend from control section 10. Remote switches 28 may be used to control auxiliary equipment.

A boot 30 proceeds distally from control section 10. An instrument channel port 32 opens into boot 30 allowing introduction of instruments into endoscope 14. The biopsy valve 34 seals instrument channel port 32. A narrow, flexible opening within biopsy valve 34 allows instruments to pass while providing a gas-tight seal around the instruments. A valve cap 36 seals biopsy valve 34 when there is no instrument within the opening of biopsy valve 34.

The working length 44 extends distally from boot 30. Working length 44 can be approximately a meter long, and has flexibility to move through body lumens such as the esophagus or lower intestines. An instrument channel 42 is open through the entire length of working length 44, opening proximally at instrument channel port 32. Fiber optics for illumination and visualization of the area distal to endoscope 14 also are within working length 44.

FIG. 1 shows universal cord 104 extending from grip section 12. Universal cord 104 carries fiber optics and a suction tube. A light source 106 for illuminating an area distal to the distal end of endoscope 14 connects to endoscope 14 using fiber optics within universal cord 104. Video monitor 110 connects through fiber optics within universal cord 104. Video monitor 110 may be controlled through an attached video system center 111. Video monitor 110, light source 106, and video system center 111 may be operable from remote switches 28 and are used to view and photograph areas distal to endoscope 14. A suction pump 108 is connected as well through universal cord 104 and is used to pull a vacuum through instrument channel 42. Suction pump 108 has a collection jar 65 to receive tissue samples that have been pulled through instrument channel 42 by suction. Equipment such as suction pump 108, light source 106, video monitor 110, and video system center 111 may also be purchased through Olympus America, Inc., in Melville, N.Y.

FIG. 1 further depicts a biopsy forceps device 37 assembled to endoscope 14. Biopsy forceps device 37 has an interior forceps half 50 and an exterior forceps half 56. Interior forceps half 50 provides a first handle 123 with a first plunger 38 at the end of an interior flexible member 58 to move interior flexible member 58 proximally and distally. Interior forceps half 50 is inserted into instrument channel port 32 and through instrument channel 42 within endoscope 14. Exterior forceps half 56 provides a second handle 125 with a second plunger 62 to move an exterior flexible member 64 proximally and distally. Exterior forceps half 56 is located alongside endoscope 14 and may be held in place with attachment bands 40. Exterior flexible member 64 can move proximally and distally through attachment bands 40.

Interior flexible member 58 and exterior flexible member 64 each can be provided with a junction 67. Each junction 67 may have suction pump 108 attached to pull a vacuum through interior flexible member 58 or exterior flexible member 64 to collection jar 65. Alternatively, each junction 67 may have an irrigation water supply attached to provide irrigation water. A plug 73 may be inserted into each junction 67, as shown in FIG. 1, to seal interior flexible member 58 and exterior flexible member 64 when no external device is attached.

Figure 2:
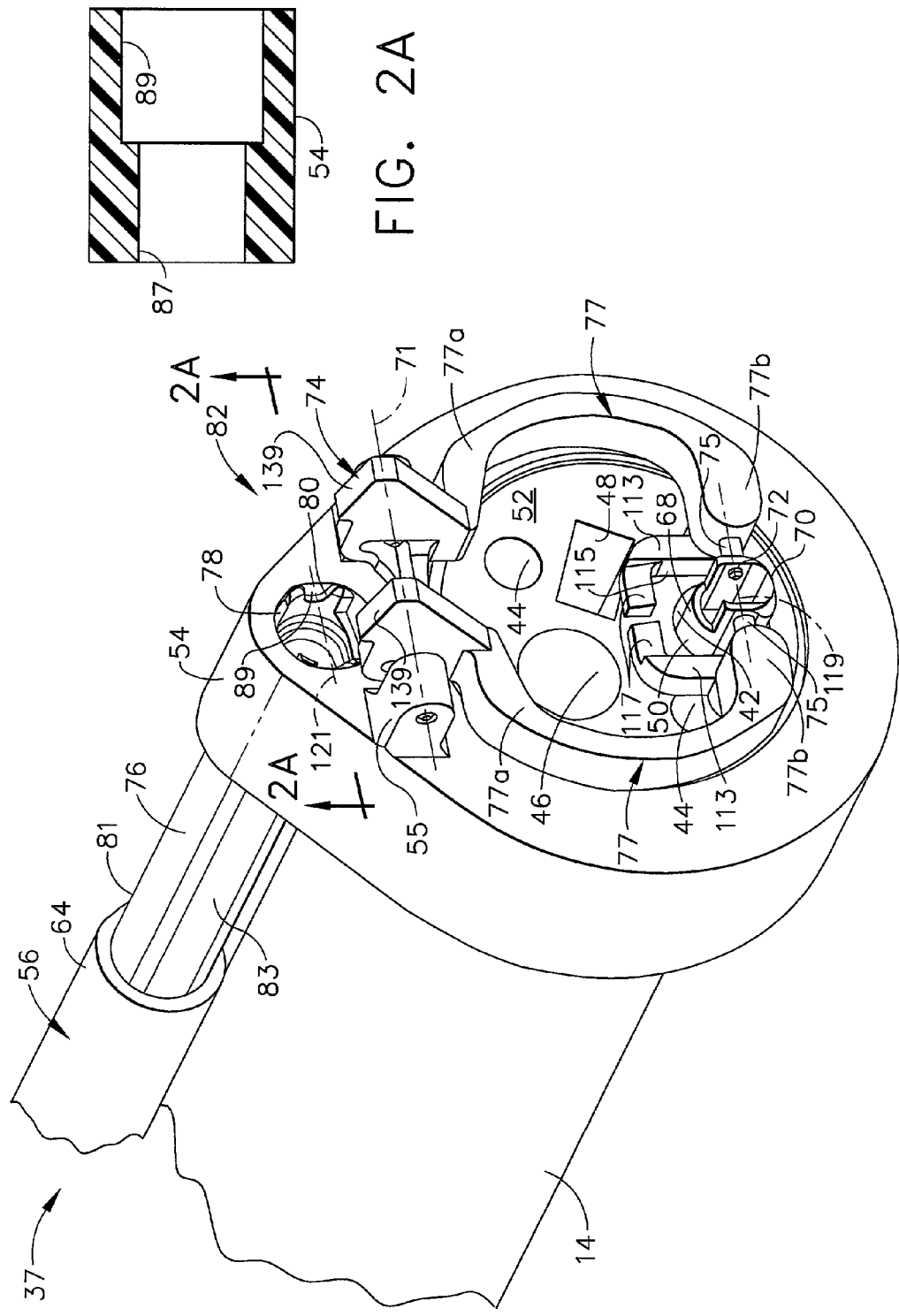
FIG. 2 is an isometric view showing the distal end of the endoscope and assembly seen in FIG. 1.

FIG. 2 depicts the distal end of endoscope 14. Distal face 52 is positioned at the distal end of endoscope 14 and provides associated elements for visualization and medical therapy. Instrument channel 42 opens at distal face 52 of endoscope 14. Light guide lenses 44, for allowing illumination of the work area, are also shown on distal face 52 of endoscope 14. An objective lens 46, placed on distal face 52 of endoscope 14, receives light from the work area and transmits an image to video monitor 110 (FIG. 1). An air/water nozzle 48 is located at the distal end of endoscope 14 adjacent to objective lens 46. Air/water nozzle 48 directs air and water onto objective lens 46 to defog and clean objective lens 46.

According to the present invention, a device, such as a mechanism, can be associated with the distal end of the endoscope 14, the device for guiding a flexible instrument extending from an instrument channel in the endoscope. As used herein, the term "mechanism" refers to devices having one or more movable members, which members can be relatively rigid or relatively flexible. Such mechanisms include, without limitation: simple mechanical devices, such as linkages (e.g. single and multiple link members wherein the links are pivotably connected to one another or a base, including four bar linkages, six bar linkages, linkages that include both hinged connections and sliding interfaces), as well as more complex mechanical devices such as telescoping devices, expanding scissors devices, devices which incorporate sliding interfaces, ball and socket joints, universal joints, or other complex connections between members.

According to one embodiment of the present invention, a pivot-arm base 54 is disposed at the distal end of the endoscope 14, and can surround the distal end of endoscope 14. Pivot-arm base 54 can be releasably joined to the distal end of the endoscope 14, such as with a light press fit, threaded engagement, snap fit, or by other suitable means. Pivot-arm base 54 can be releasably joined to the distal end of the endoscope 14 so that the pivot arm base 54 and its associated assembly can be removed from the endoscope between operating procedures, such as for cleaning, sterilization, addition of instruments, and the like. Alternatively, Pivot-arm base 54 can be fixedly attached to the distal end of the endoscope 14.

Pivot arm 74 connects to pivot-arm base 54 by, for example, pins placed through bosses 55 raised on pivot-arm base 54 and pivot arm 74 rotates about pivot axis 71. Pivot-arm stops 139 can be disposed on pivot arm 74 to contact pivot-arm base 54 for limiting the angle through which pivot arm 74 rotates about axis 71. In the embodiment illustrated in FIG. 2, a substantially rigid pivot arm 74 is shown having two curved support halves 77. Each support half 77 of pivot arm 74 extends from a proximal end 77a adjacent axis 71 to a distal end 77b. The distal ends 77b can be opposed as shown in FIG. 2. Each support half 77 can be shaped in an arcuate fashion to be curved away from the line of sight of objective lens 46 to avoid obstructing the view seen by the physician through objective lens 46. A stepped-diameter pin 75 extends from the unattached distal end 77b of each support half 77 of pivot arm 74, with the larger diameter of each stepped-diameter pin 75 nearer support half 77 than the smaller diameter. Guide tabs 113 can be located at the distal ends 77b of support halves 77 adjacent stepped-diameter pins 75. Guide tabs 113 can include longitudinal ramp surfaces 115 for positioning mating parts longitudinally, and radial ramp surfaces 117 for radially positioning mating parts, as described below.

Pivot arm 74 together with pivot-arm base 54 are illustrated in the figures as end cap 82. End cap 82 comprising base 54 and pivot arm 74 can be manufactured as a unit for assembly to endoscope 14. End cap 82 can be reusable after sterilization, or alternatively, end cap 82 could be disposable. End cap 82 can be made from, for example, a plastic such as polycarbonate or a metal such as stainless steel. Alternatively, a manufacturer of endoscope 14 could integrate pivot arm 74 with endoscope 14.

End cap 82, comprising base 54 and pivot arm 74, can be provided in sterile packaging. At the time of the medical procedure, the end cap 82 can be removed from the sterile packaging and be joined to the distal end of the endoscope.

FIG. 2 further shows interior forceps half 50 proceeding from instrument channel 42. Interior forceps jaw 68 can attach to the end of interior flexible member 58 by a press fit into the inner diameter of interior flexible member 58. Interior forceps jaw 68 has a first sharp edge 70 and two engagement holes 72 for insertion of the smaller diameter of stepped-diameter pins 75. Interior forceps jaw 68 and interior flexible member 58 both have open interior portions, creating a hollow tubular structure through which gas, fluids, particulate matter, or instruments may pass through to the proximal end. Interior flexible member 58 may have a spring placed within the structure to support the walls of interior flexible member 58 while still allowing flexibility. Pivot arm 74 as depicted in FIG. 2 is rigid enough to resist substantial unwanted deflection caused by bending, torsion, and compression loading applied by tissue and interior flexible member 58.

FIG. 2 further depicts pivot arm 74 connecting to interior forceps half 50. In the embodiment shown in FIG. 2, pivot arm 74 has two connected support halves 77 engaged with stepped-diameter pins 75 to interior forceps jaw 68, capturing interior forceps jaw 68 to pivot arm 74. Stepped-diameter pins 75 align with each other, creating a first axis of rotation 119. Interior forceps jaw 68 can rotate freely relative to pivot arm 74 about first axis of rotation 119, but the rigidity of pivot arm 74 restricts rotation of interior forceps jaw 68 about the longitudinal axis of interior forceps jaw 68.

FIG. 2 also shows the distal end of exterior forceps half 56 aligned alongside endoscope 14 and secured by pivot-arm base 54. Exterior forceps half 56 possesses an exterior forceps jaw 76 affixed at the distal end of exterior flexible member 64. Exterior forceps jaw 76 may be attached, for example, by fashioning a connector portion 81 to extend proximally to press-fit into the inner diameter of exterior flexible member 64. Connector portion 81 has flats 83 on each side to engage a double-D hole 87, depicted in cross-section in FIG. 2A, on pivot-arm base 54. Connector portion 81 can slide linearly through double-D hole 87, but cannot rotate about the longitudinal axis of exterior forceps jaw 76. Flats 83 on connector portion 81 abut the flat sides of double-D hole 87 to resist such rotation. Exterior forceps jaw 76 and exterior flexible member 64 are both open in their interior portions, creating a tubular structure so that gas, fluids, particulate matter, or instruments may pass through to the proximal end. Exterior flexible member 64 may also have a spring placed internally for support of the outer wall.

Exterior forceps jaw 76 provides a second sharp edge 78 and engagement notches 80. Second sharp edge 78 is used with first sharp edge 70 for tissue cutting, and engagement notches 80 connect with the larger diameters of stepped-diameter pins 75 to form a biopsy forceps as will be described. Engagement notches 80 align with each other near the distal end of exterior forceps jaw 76 to define a second axis of rotation 121. Interior forceps jaw 68 rotates relative to exterior forceps jaw 76 about second axis of rotation 121.

Figure 3:
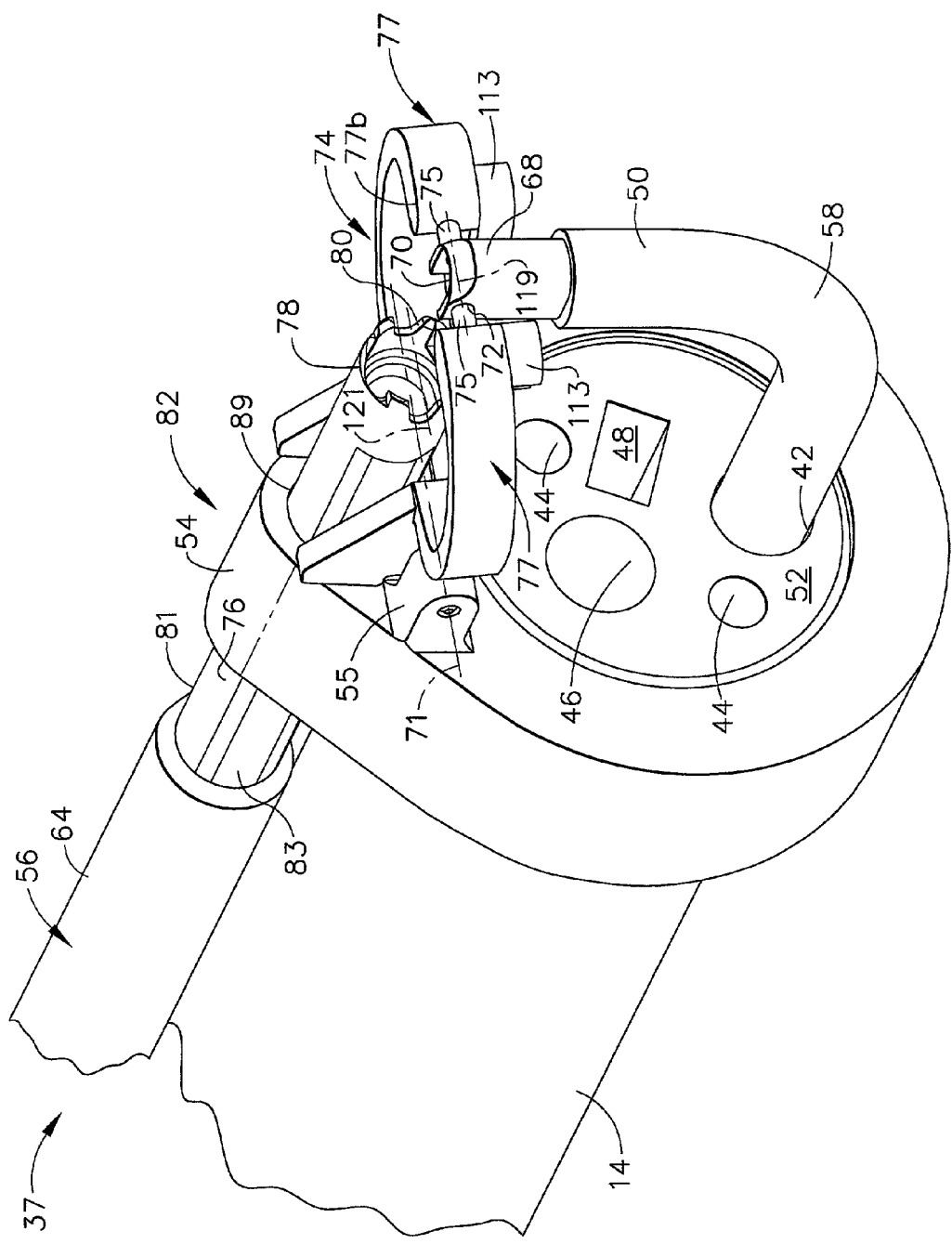
FIG. 3 is an isometric view of the endoscope and assembly seen in FIG. 1 with the interior flexible member extended and curved through about approximately ninety degrees with respect to the endoscope.

FIG. 3 further shows the distal end of endoscope 14 equipped with end cap 82 and biopsy forceps device 37. In FIG. 3, interior flexible member 58 is seen extended and curved through about approximately ninety degrees. To provide the assembly shown in FIG. 3, a physician or other use can first attach end cap 82 to the distal end of endoscope 14. Interior forceps half 50 can be inserted through instrument channel port 32 (FIG. 1) and into instrument channel 42. At the distal end of instrument channel 42, pivot arm 74 can be connected to interior forceps jaw 68 by insertion of the smaller diameters of stepped-diameter pins 75 into engagement holes 72. Insertion of stepped-diameter pins 75 into engagement holes 72 may be accomplished, for example, by spreading support halves 77 and positioning engagement holes 72 of interior forceps jaw 68 in between support halves 77. Support halves 77 may then be allowed to return back to their relaxed position to move the smaller diameters of stepped-diameter pins 75 into engagement holes 72. Alternatively, stepped-diameter pins may be spring loaded, such as in the fashion of watch band connection pins.

Exterior forceps half 56 is attached alongside endoscope 14 using pivot-arm base 54. In the embodiment depicted in FIG. 3, exterior forceps half 56 slips into double-D hole 87 from the distal side. Exterior flexible member 64, carrying proximally-attached second handle 125, press-fits over connector portion 81 to complete the assembly of exterior forceps half 56. Exterior forceps half 56 may be additionally secured to endoscope 14 using attachment bands 40. Exterior flexible member 64 can be slipped through attachment bands 40.

Endoscope 14, end cap 82, and biopsy forceps device 37 are inserted into a body near tissue to be examined or treated. The assembly may be inserted into, for example, a body lumen such as the esophagus or large intestine.

After the device is inserted into the body, first plunger 38 (FIG. 1) is depressed extending interior flexible member 58 through instrument channel 42. Pivot arm 74 restrains the distal end of interior flexible member 58 to travel substantially in an arc, curving interior forceps jaw 68 towards a position distal to distal face 52 of endoscope 14 and on the outer periphery of endoscope 14. Pivot arm 74 substantially prevents twisting of interior flexible member 58 around the longitudinal axis of interior flexible member 58. Pivot-arm stops 139 contact pivot-arm base 54 to prevent over-rotation of pivot arm 74. In the position shown in FIG. 3, interior flexible member 58 and associated forceps jaw 68 have moved substantially through an arc of about approximately ninety degrees. Interior forceps jaw 68 is now in a position visible through video monitor 110 (FIG. 1) utilizing light received from objective lens 46. The physician may photograph the work site using photographic equipment available with video system center 111. The physician may also use computer equipment to process images received from the work site. The physician may maneuver interior forceps jaw 68 to a position to take tissue, such as a polyp, from a biopsy site.

Figure 4:
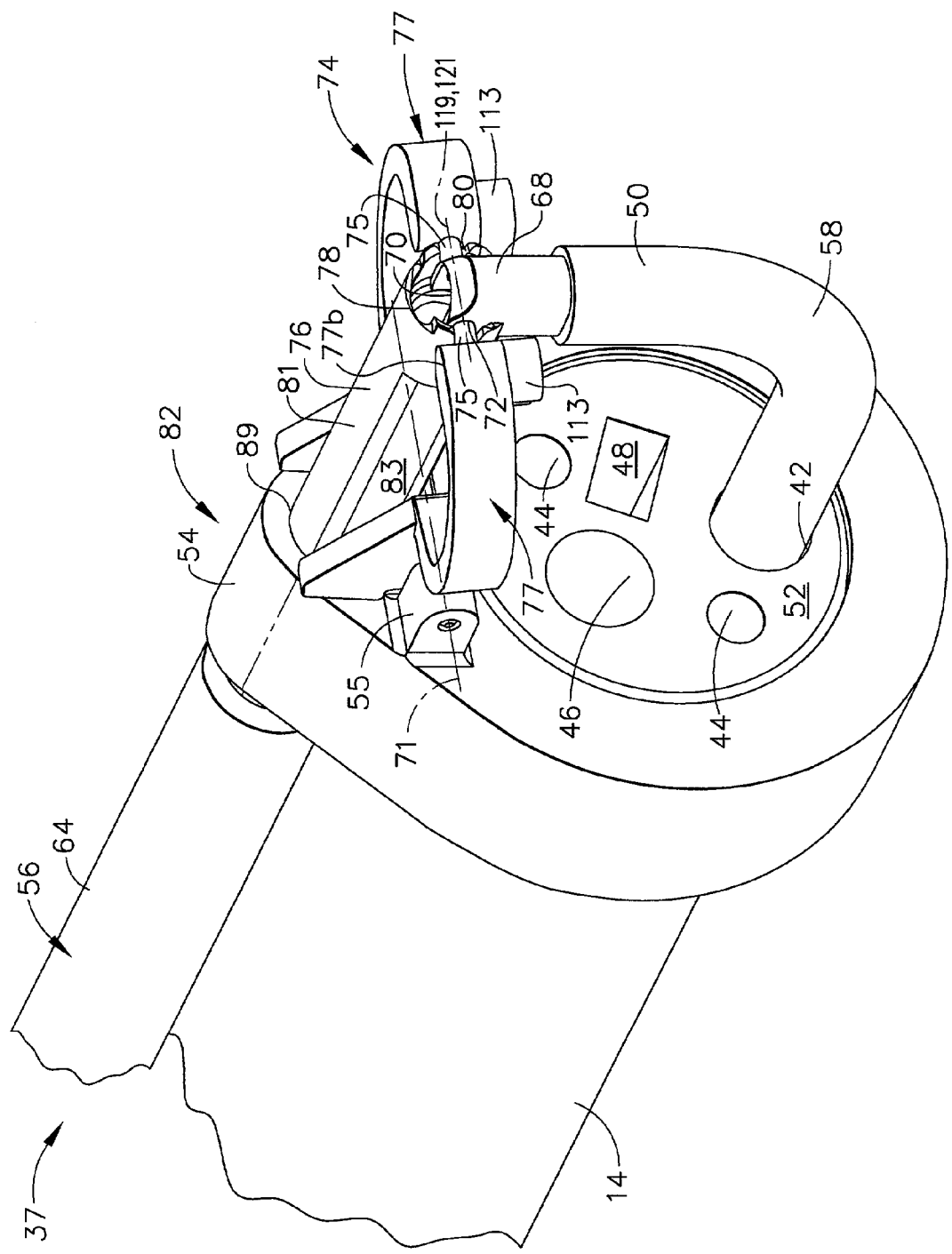
FIG. 4 is an isometric view of the endoscope and assembly seen in FIG. 1 with the interior flexible member extended and curved through about approximately ninety degrees with respect to the endoscope and the exterior flexible member extended to cooperate with the interior flexible member.

FIG. 4 shows exterior forceps jaw 76 extending from distal attachment collar 54. Second plunger 62 (FIG. 1) is depressed to move exterior flexible member 64 and exterior forceps jaw 76 distally. As exterior forceps jaw 76 extends distally from pivot-arm base 54, longitudinal ramps 115 and radial ramps 117 effectively guide exterior forceps jaw 76 into position to connect to stepped-diameter pins 75. Engagement notches 80 on exterior forceps jaw 76 engage the larger diameter of stepped-diameter pins 75, rotatably connecting interior forceps jaw 68 to exterior forceps jaw 76. The two different diameters of stepped-diameter pins 75 align, so that in the illustrated embodiment first axis of rotation 119 and second axis of rotation 121 coincide. First axis of rotation 119 of interior forceps jaw 68 about pivot arm 74 and second axis of rotation 121 of interior forceps jaw 68 about exterior forceps jaw 76 lie on the same line. Accordingly, jaw 68 rotates relative to jaw 76 about the same axis that jaw 68 rotates about pivot arm 74.

Figure 5:
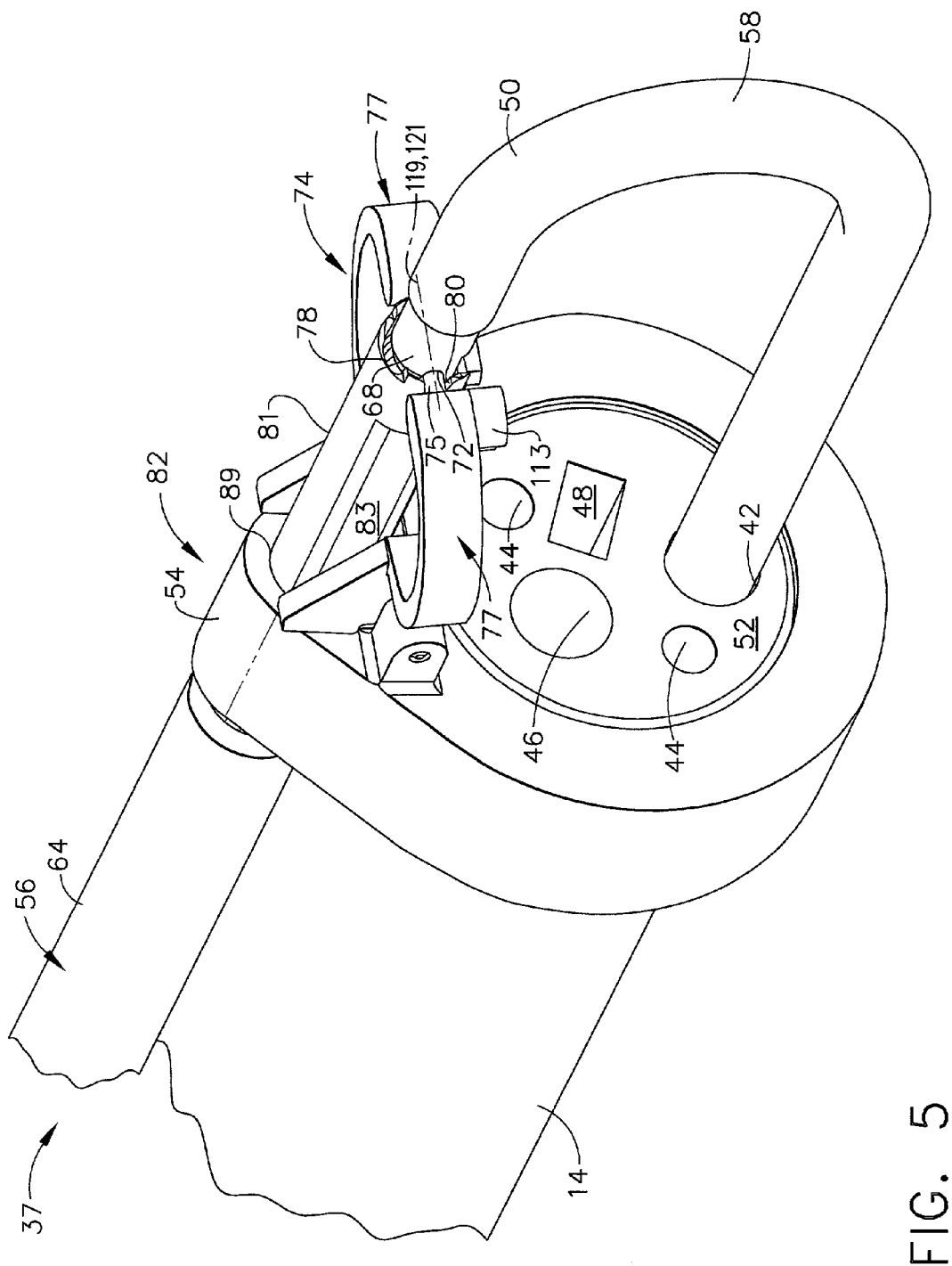
FIG. 5 is an isometric view of the endoscope and assembly seen in FIG. 1 with the interior flexible member extended and curved through about approximately one hundred eighty degrees with respect to the endoscope and the exterior flexible member extended to cooperate with the interior flexible member.

FIG. 5 shows interior forceps jaw 68 rotated into a closed position. First plunger 38 is depressed further to rotate interior flexible member 58 and associated interior forceps jaw 68 through an additional ninety degrees to about approximately one hundred eighty degrees of rotation. First sharp edge 70 and second sharp edge 78 can move past each other and can take a biopsy sample in moving to the illustrated position.

Because exterior flexible member 64 has an open interior portion, suction pump 108 may be used through a junction open into exterior forceps half 56 to apply suction through the exterior flexible member 64. The biopsy sample or tissue sample can be suctioned away from the biopsy site. The applied suction can pull a biopsy sample through exterior flexible member 64 to the proximal end of endoscope 14 and out of endoscope 14. The biopsy sample may be suctioned into collection jar 65 and taken for analysis. Alternatively, interior forceps half 50 could use collection jar 65 and attached suction pump 108 to collect biopsy samples as well. Suction may be applied from a junction 67 open into the proximal end of interior flexible member 58 to pull a biopsy sample through interior flexible member 58. Alternatively, an irrigation solution such as water could be provided from the proximal end of one of either interior forceps half 50 or exterior forceps half 56 to flow through the loop created by the closed jaw halves. The flow of irrigation solution could then force a tissue sample through the other forceps half for collection.

These methods enable more than one tissue sample to be taken before removing biopsy forceps device 37 from the body. Moving the sample away from the biopsy site, such as by vacuum, frees biopsy forceps device 37 to take another sample.

Features of pivot arm 74 make it useful for a variety of applications. First, pivot arm 74 can be used to constrain motion of the distal end of interior flexible member 58 to find predictably the same tissue area of interest. This useful attribute enables instruments intended to cooperate with interior flexible member 58, such as external forceps jaw 76, to be repeatably placed at a tissue site that would normally be difficult to repeatably access.

Figure 7:
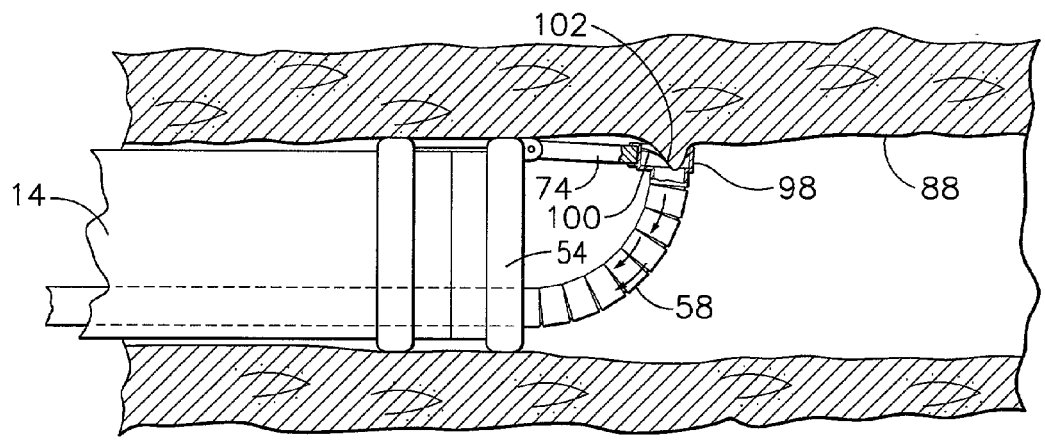
FIG. 7 is a side view of another embodiment of an end cap having a bladed pivot arm utilizing an interior flexible member having suction to pull tissue towards the blade.

Second, pivot arm 74 can restrain motion of the distal end of interior flexible member 58 along a predetermined path, such as along arc. In the embodiment shown, the distal end of the flexible member 58 can be constrained in translation to cause interior flexible member 58 to curve through an arc of 90 degrees or greater to approach tissue spaced from the distal end of the endoscope and associated with the periphery of endoscope 14 (such as is shown in FIG. 7). In particular, the pivot arm 74 permits positioning of the distal end of the flexible member 58 at a tissue site that is adjacent the distal end of the endoscope, yet offset from the longitidunal axis of the endoscope a distance at least as great as the radius of the endoscope. Accordingly, tissue sites adjacent the distal end of the endoscope and associated with the perimeter of the endoscope can be accessed in a repeatable fashion.

Third, as illustrated in FIG. 5, the pivot arm can guide internal flexible member 58 to curve through an arc of about approximately 180 degrees to face towards distal face 52 of endoscope 14. Guiding the internal flexible member 58 to bend through an arc of about 180 degrees allows the distal end of flexible member 58 and any associated medical instrument to face the camera or other visualization device associated with the distal end of the endoscope. Accordingly, the user can more readily view various aspects of treatment provided by the flexible member 58.

Fourth, because first axis of rotation 119 coincides with the second axis of rotation 121, the need for interior forceps jaw 68 to translate relative to pivot arm 74 when cooperating with exterior forceps jaw 76 is eliminated. Cooperative work can be accomplished by simple rotation of interior forceps jaw 68 once interior forceps jaw 68 is joined to exterior forceps jaw 76.

Figure 6:
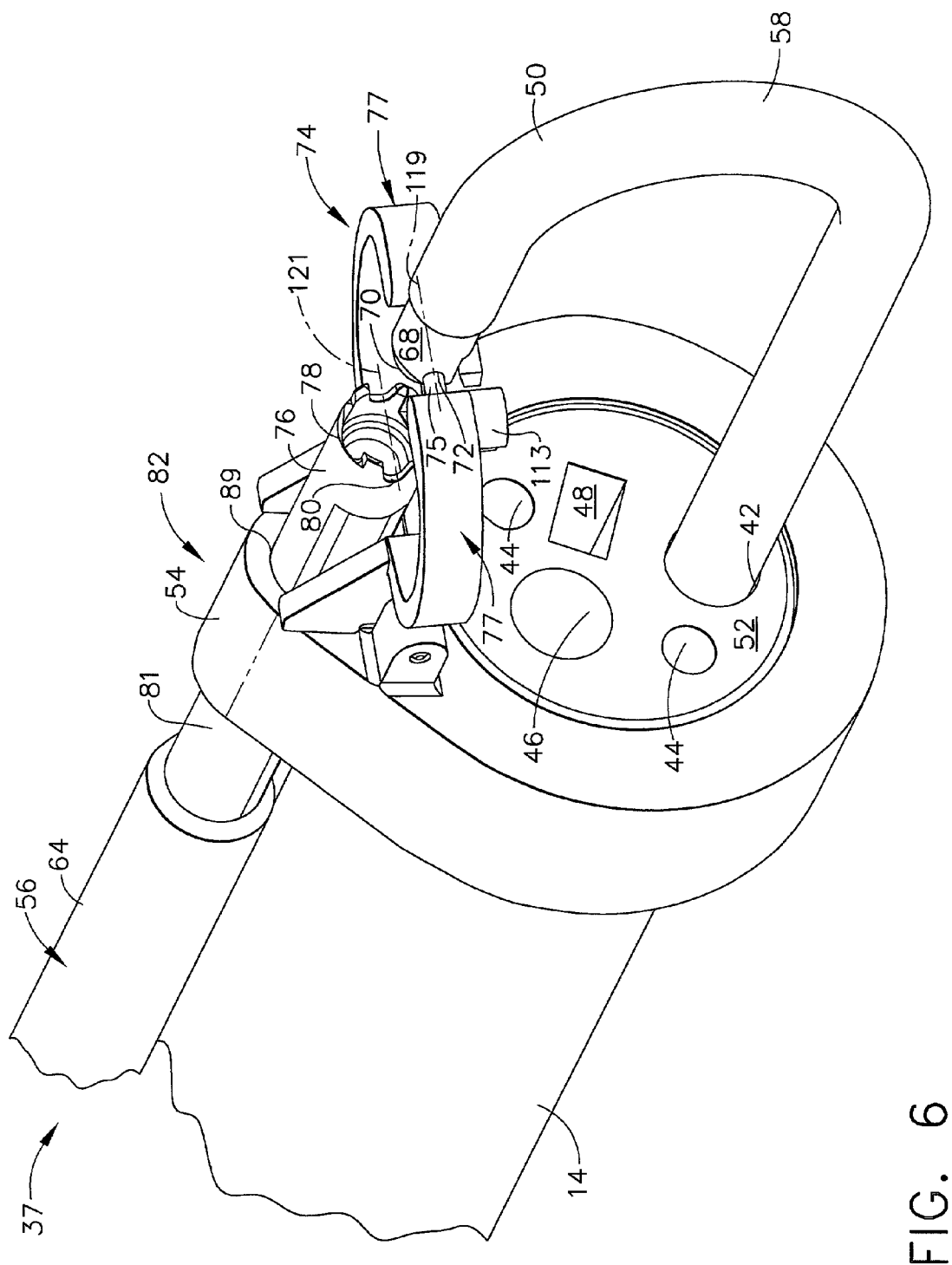
FIG. 6 is an isometric view of the endoscope and assembly seen in FIG. 1 with the interior flexible member extended and curved through about approximately one hundred eighty degrees with respect to the endoscope and the exterior flexible member slightly retracted proximally from the position shown in FIG. 5.

FIG. 6 illustrates exterior forceps jaw 76 and interior forceps jaw 68 disengaged. After a biopsy sample has been taken, a physician moves second plunger 62 (FIG. 1) proximally to retract exterior flexible member 64 and exterior forceps jaw 76 proximally to disengage exterior forceps jaw 76 from interior forceps jaw 68. The physician also retracts interior flexible member 58 by moving first plunger 38 (FIG. 1) proximally. Interior flexible member 58 moves through an arc as it retracts into instrument channel 42. Interior flexible member 58, using interior forceps jaw 68, rotates pivot arm 74 to return back to the position parallel to distal face 52 of endoscope 14. The physician may withdraw endoscope 14 from the patient, or the physician may choose another area of tissue within the patient to biopsy. The physician does not need to withdraw any portion of biopsy forceps device 37 from the body before taking another specimen of tissue.

Different methods of tissue biopsy can be performed on tissue using end cap 82 attached to an interior flexible member 58. FIG. 7 shows an example of a rigid pivot arm 74 equipped with a ring 98 containing a blade 100. The embodiment of pivot arm 74 shown in FIG. 7 is pivotally attached to pivot-arm base 54. Pivot arm 74 of FIG. 7 is rigid enough to prevent substantial deflection caused by bending, torsion, and compression loading applied by tissue and interior flexible member 58. Pivot arm 74 of FIG. 7 could be made of, for example, aluminum or an engineering plastic such as polycarbonate.

FIG. 7 further illustrates that blade 100 could fit substantially within ring 98 leaving an opening through which a tissue sample could pass. Interior flexible member 58 assembles to pivot arm 74 using, for example, a press fit into an extension from ring 98. As illustrated in FIG. 7, interior flexible member 58 could be a tube through which suction may be applied. Blade 100 slants proximally towards interior flexible member 58 to assist in cutting or tearing tissue for biopsy, and blade 100 possesses a knife edge 102.

FIG. 7 shows an embodiment of interior flexible member 58 attached to ring 98 of pivot arm 74 and extended to a position adjacent a wall of body lumen 88. As shown in FIG. 7, the pivot arm 74 can provide repeatable positioning of the distal end of the flexible member 58 at a tissue site that is adjacent the distal end of the endoscope, and radially offset from the longitudinal centerline of the endoscope a distance at least as great as the radius of the endoscope. Accordingly, the mechanism according to the present invention allows repeatable access to tissue sites on a body lumen wall adjacent the distal end of the endoscope.

Figure 8:
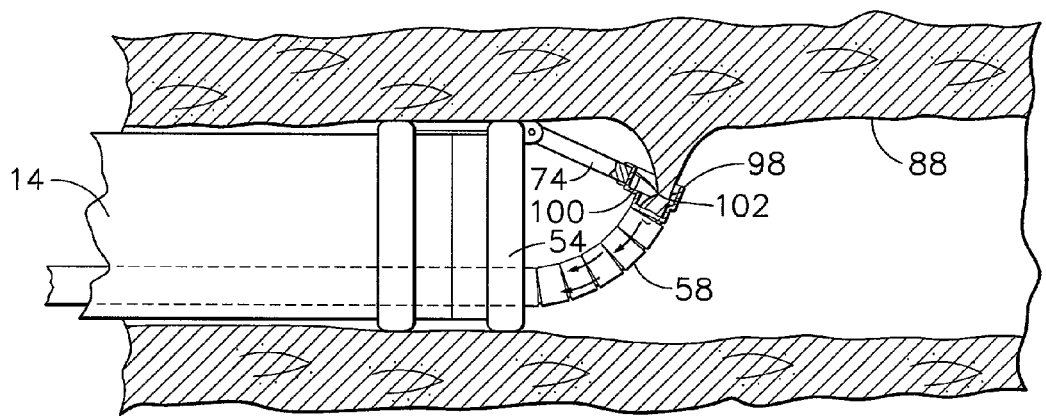
FIG. 8 is a side view of the end cap of FIG. 7 with the interior flexible member retracting to take a biopsy sample.
Figure 9:
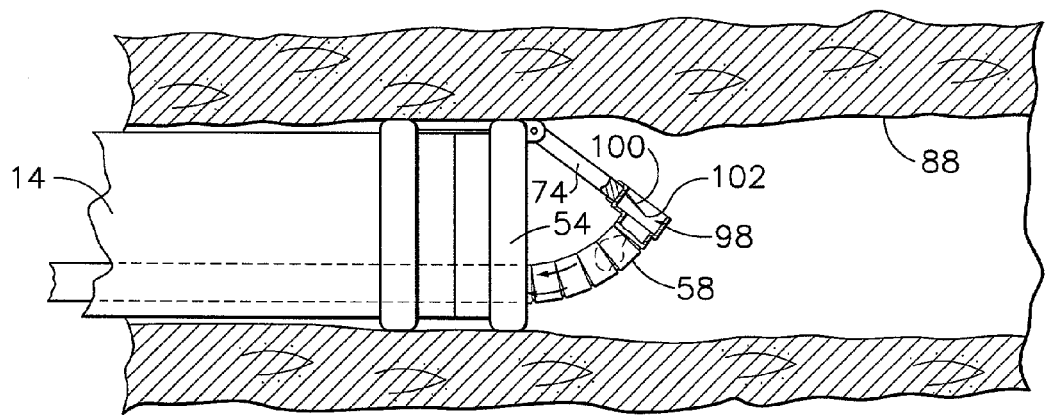
FIG. 9 is a side view of the end cap of FIG. 7 with the biopsy sample being evacuated away from the work area through the interior flexible member.

Suction applied to interior flexible member 58 could pull tissue past blade 100 and into ring 98. Pivot arm 74 can then be retracted, as shown in FIG. 8, by retracting interior flexible member 58 while suction continues through interior flexible member 58. Retraction of pivot arm 74 can cause tissue to pull on blade 100 against the proximal slant of blade 100. Edge 102 of blade 100 can then cut and tear a tissue biopsy sample to be retrieved by the suction applied through interior flexible member 58, as shown in FIG. 9. If needed, a slight proximal and distal movement of endoscope 14 can help edge 102 cut and tear tissue to be removed. Because the tissue sample has been evacuated away from the biopsy site, another biopsy may then be performed without removing interior flexible member 58 or endoscope 14 from the body.

Figure 10:
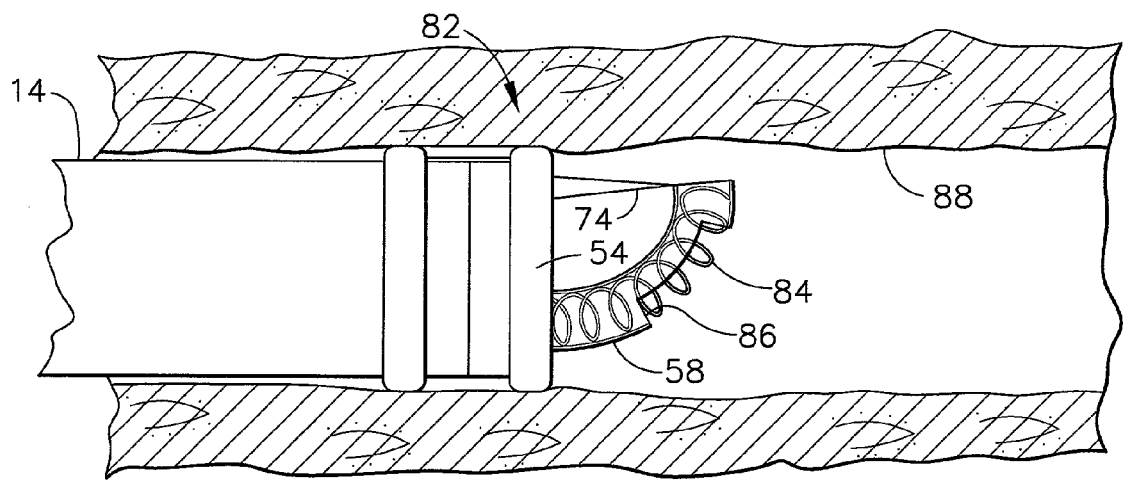
FIG. 10 is a side view of an embodiment of an end cap cooperating with an interior flexible member having a conductive wire through which RF current may be applied with the flexible member curved through about approximately ninety degrees with respect to the endoscope.

It will be recognized that equivalent structures may be substituted for the structures illustrated and described herein and that the described embodiment of the invention is not the only structure which may be employed to implement the claimed invention. As one example of an equivalent structure which may be used to implement an embodiment of the present invention, pivot arm 74 may be created from a flexible strand such as a suture, wire, or string. FIG. 10 shows two such strands extending from interior flexible member 58 to connect with pivot-arm base 54 to create an equivalent structure of end cap 82. Tension in the strands of the embodiment of pivot arm 74 shown in FIG. 10 restrains interior flexible member 58 to angulate towards tissue distal to and at the periphery of endoscope 14. Additionally, because the embodiment of pivot arm 14 depicted in FIG. 10 consists of two flexible strands under tension, interior flexible member 58 is placed at an apex of a triangular structure. The two strands under tension direct flexible member 58 to a specific point along the periphery of endoscope 14.

Other apparatus may be envisioned to substitute for end cap 82. For example, end cap 82 may comprise a base 54 or an equivalent structure supporting an equivalent mechanism for pivot arm 74. For example, base 54 may become a spring clamp held by spring force to endoscope 14 while carrying a four-bar linkage. The four-bar linkage, by way of further example, can be a substitute mechanism for pivot arm 74 to maneuver or guide an instrument. A mechanism such as pivot arm 74 may attach directly to endoscope 14 without the use of a base or its equivalent, making the mechanism the entire apparatus for maneuvering or guiding an instrument.

As a further example of equivalent structures that may be used to implement the present invention, different end-effectors to perform different types of therapy on tissue are seen.

Figure 11:
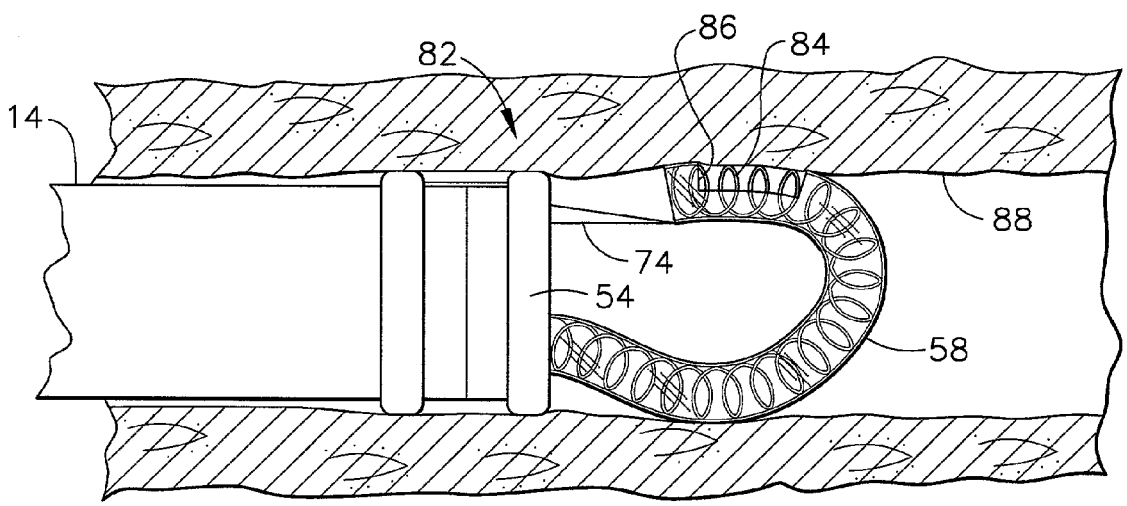
FIG. 11 is a side view of the end cap and flexible interior member of FIG. 10 with the flexible interior member curved through about approximately one hundred eighty degrees with respect to the endoscope.

FIG. 10 and FIG. 11 show pivot arm 74 of end cap 82 attached to interior flexible member 58 containing a coil spring 84. Interior flexible member 58 may be transparent to allow visualization of coil spring 84. An opening 86 in the wall of interior flexible member 58 exposes a portion of coil spring 84 to a side wall of a body lumen. Coil spring 84 can extend proximally through endoscope 14 to the proximal end where an attachment to a generator produces RF current. RF current may be applied through coil spring 84 to a wall of the body lumen in a specific area distal to endoscope 14 to cause ablation of tissue for therapeutic value. Alternatively, two insulated wires could be utilized to provide bipolar RF current. The wires could end in electrodes placed at opening 86.

Figure 12:
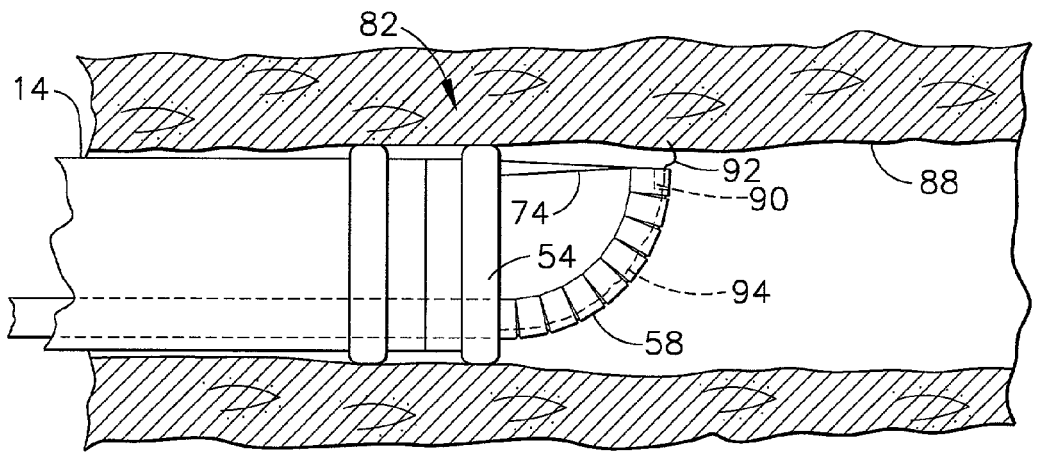
FIG. 12 is a side view of an embodiment of an end cap with an interior flexible member carrying a suture and thread and curved through an angle of about approximately ninety degrees with respect to the endoscope.
Figure 13:
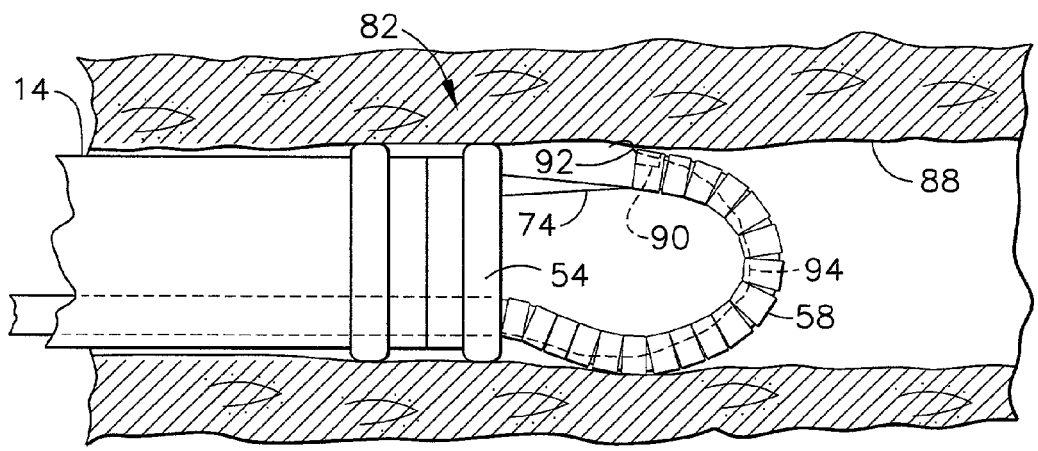
FIG. 13 is a side view of the end cap and interior flexible member of FIG. 12 with the interior flexible member curved through an angle of about approximately one hundred eighty degrees with respect to the endoscope to suture tissue.
Figure 14:
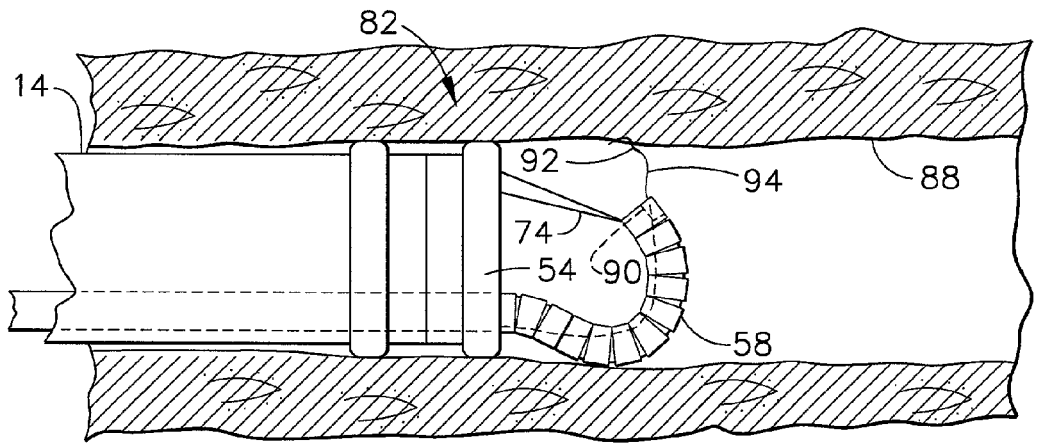
FIG. 14 is a side view of the end cap and interior flexible member of FIG. 12 with the interior flexible member retracting.

FIGS. 12 through 14 show an example of suturing through the open interior portion of an extended interior flexible member 58. Interior flexible member 58 may be formed from a spring with a thin plastic sleeve covering. A needle 92 carrying suture 94 may be used through interior flexible member 58. A needle retainer 90 is fashioned at the distal end of interior flexible member 58. Needle retainer 90 may be, for example, a small tube attached at the distal end of interior flexible member 58 and having an interior diameter slightly smaller than needle 92. Needle 92 is secured within needle retainer 90 by the friction of a press fit between needle 92 and needle retainer 90. Suture 94 trails proximally through interior flexible member 58 to a useful and convenient length. End cap 82 with pivot arm 74 is attached to the distal end of endoscope 14.

A physician can attach suture 94 to needle 92, insert needle 92 into needle retainer 90 and extend suture 94 proximally through interior flexible member 58. End cap 82 is then connected to the distal end of endoscope 14, and pivot arm 74 joined with the distal end of interior flexible member 58. Interior flexible member 58 extends and travels through an arc while restrained at the distal end of pivot arm 74, carrying needle 92 to pierce the wall of body lumen 88 at a precise point. Needle 92 may be fashioned with a curvature designed to travel through the tissue of body lumen 88 and emerge at a point offset from the insertion point in a manner shown in FIGS. 12 through 14. After needle 92 has looped through tissue, interior flexible member 58 can be withdrawn to leave needle 92 within the tissue to the side of the lumen.

Figure 15:
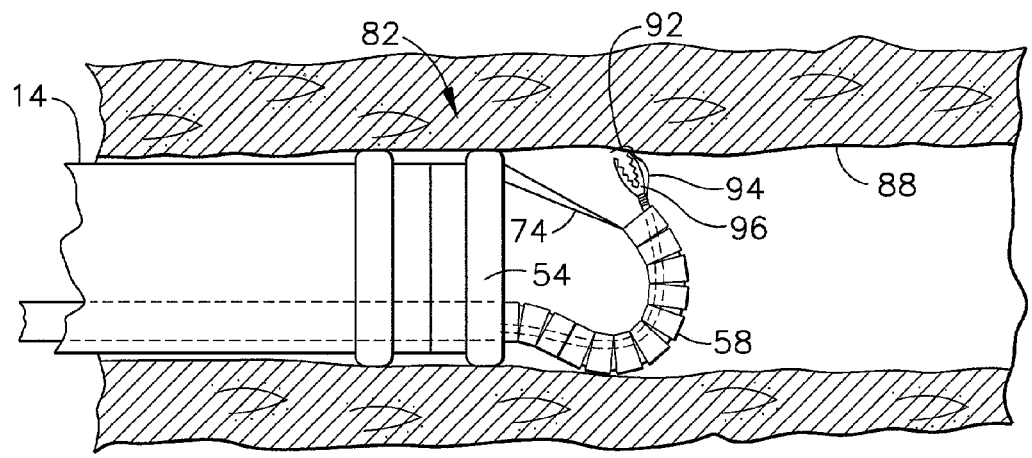
FIG. 15 is a side view of an end cap and interior flexible member with the interior flexible member having an inserted grasper.
Figure 16:
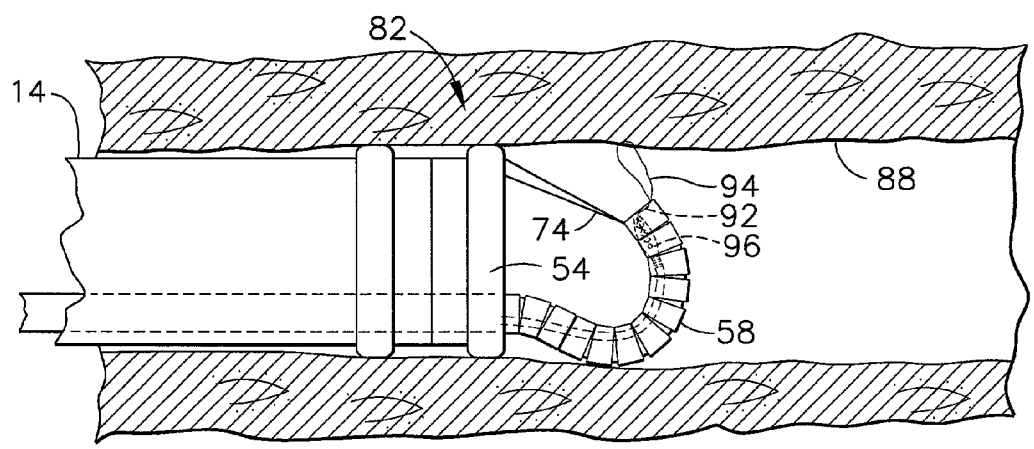
FIG. 16 is a side view of the end cap of FIG. 15 showing the grasper pulling suture through tissue.

FIGS. 15 and 16 depict grasper 96 emerging from interior flexible member 58. A suitable grasper 96 may be purchased from Microvasive Endoscopy, in Quincy, Mass. A physician may take grasper 96 and insert it through interior flexible member 58, grasp the end of needle 92, and pull suture through the opening created by the needle. To tie off the knot, a physician may place a clip on the loose threads to secure the suture.

Figure 17:
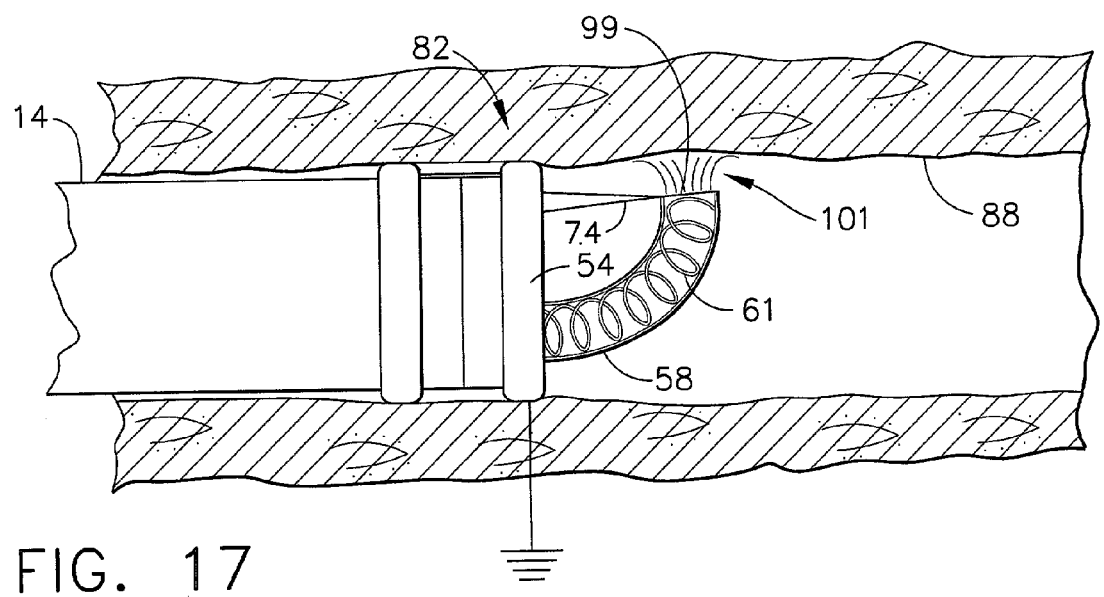
FIG. 17 is a side view of an embodiment of an end cap and an interior flexible member equipped to emit ionized argon gas from a distal port.
Figure 18:
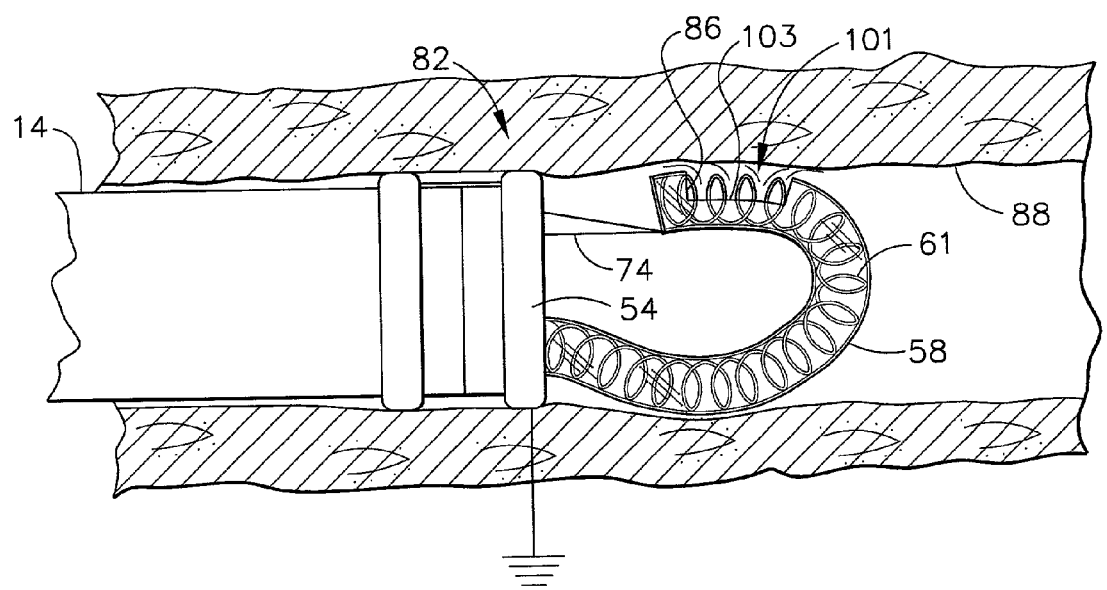
FIG. 18 is a side view of an embodiment of an end cap and an interior flexible member equipped to emit ionized argon gas from a circumferential port.

FIG. 17 shows an embodiment of a mechanism maneuvering an interior flexible member 58 that can emit ionized argon gas 101 to facilitate the flow of electrical current. A distal opening 99 to emit ionized gas may be at the distal end of flexible member 58 as shown in FIG. 17, or a circumferential opening 103 may be placed on a circumferential portion of flexible member 58 as shown in FIG. 18. Ionized argon gas 101 can coagulate large areas of tissue in a non-contact technique. After endoscope 14 is advanced into a body lumen such as the esophagus, pivot arm 74 can bend interior flexible member 58 to a point near, but not touching, the inner surface of the body lumen. A sufficient voltage is then placed across electrodes to ionize argon gas 101 proceeding from flexible member 58. In the embodiments shown in FIG. 17 and FIG. 18, interior flexible member 58 is lined with a conductive spring 61 to serve as an electrode. A return electrode is also supplied. For example, base 54 can be made of a conductive material to serve as a return electrode.

As a further example of an equivalent structure that may be used to implement the present invention, a rigid pivot arm 74 may have extensions to permit more distal movement of interior flexible member 58.

Figure 19:
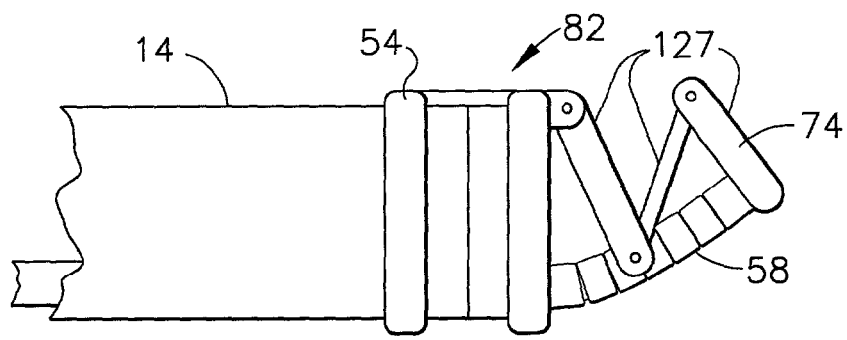
FIG. 19 is a side view of an embodiment of an end cap having a pivot arm with accordioning extensions.
Figure 20:
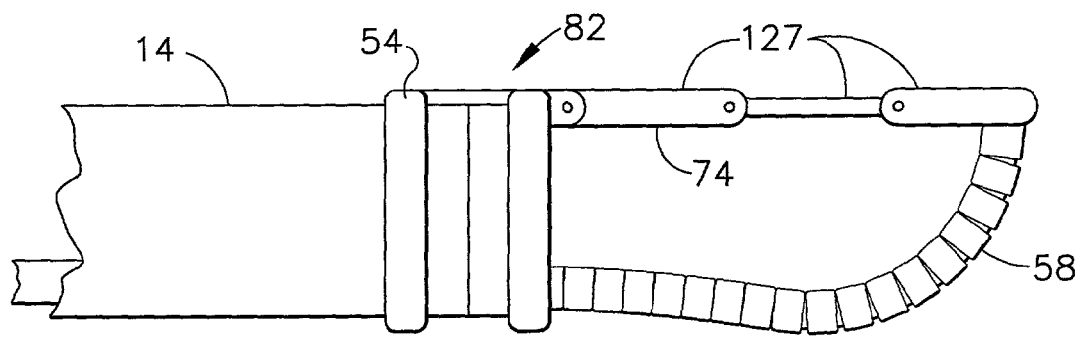
FIG. 20 is a side view of the end cap of FIG. 19 showing the pivot arm extended and the interior flexible member rotated through about approximately ninety degrees with respect to the endoscope.

FIG. 19 shows an embodiment of pivot arm 74 with rotating extensions 127 rotatably pinned to accommodate a design of pivot arm 74 that will accordion as interior flexible member 58 is moved distally. FIG. 20 shows the design of FIG. 19 in an extended position.

Figure 21:
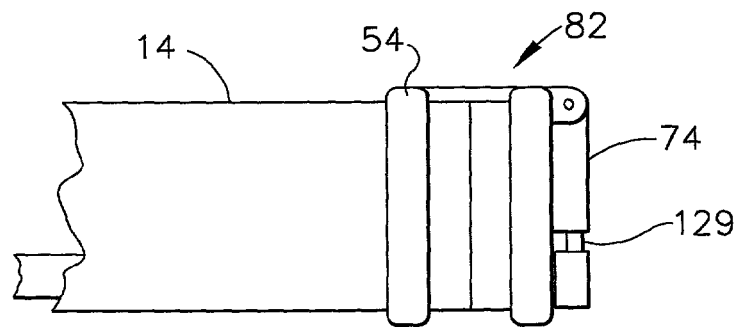
FIG. 21 is a side view of an embodiment of an end cap having a pivot arm with telescoping extensions.
Figure 22:
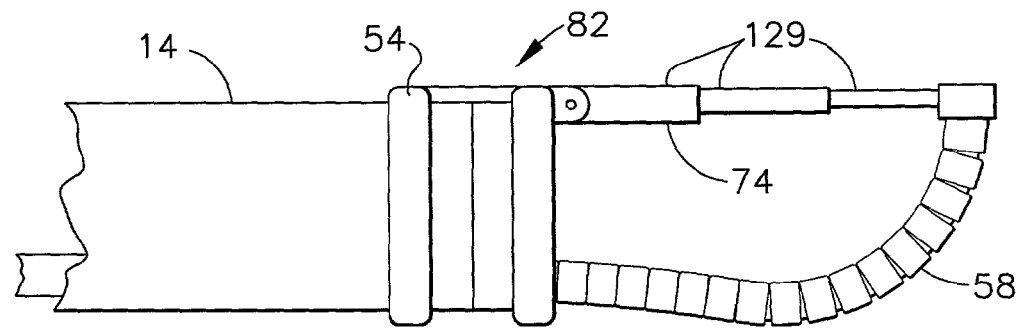
FIG. 22 is a side view of the end cap of FIG. 21 showing the pivot arm extended and the interior flexible member rotated through about approximately ninety degrees with respect to the endoscope.

FIG. 21 shows a design of pivot arm 74 that has telescoping extensions 129. FIG. 22 shows the design of FIG. 21 in an extended position.

It will become readily apparent that many other instruments may be created to take advantage of configurations of pivot arm 74. These instruments may, for example, provide injection therapy, irrigate the worksite, resect mucosa, and perform other useful functions for treatment of body tissue. Interior forceps jaw 68 or exterior forceps jaw 76 may become any interior end-effector or external end-effector for performing useful work. Internal flexible member 58 and external flexible member 64 may be any flexible members capable of maneuvering an end-effector, and each may have a handle for maneuvering and actuating its respective end-effector. A first instrument having a first handle, an internal flexible member and an internal end-effector may then be inserted through instrument channel 42 of endoscope 14 and connected to an embodiment of pivot arm 74. A second instrument may be created having a second handle, an external flexible member, and an external end-effector. The first instrument may then be used cooperatively with the second instrument inserted alongside endoscope 14 or through a second instrument channel within endoscope 14 to perform therapy. It is possible for instruments to be linked to become one instrument with two end-effectors. The instrument created by linking may have one handle with one actuation mechanism to activate both end-effectors.

Figure 23:
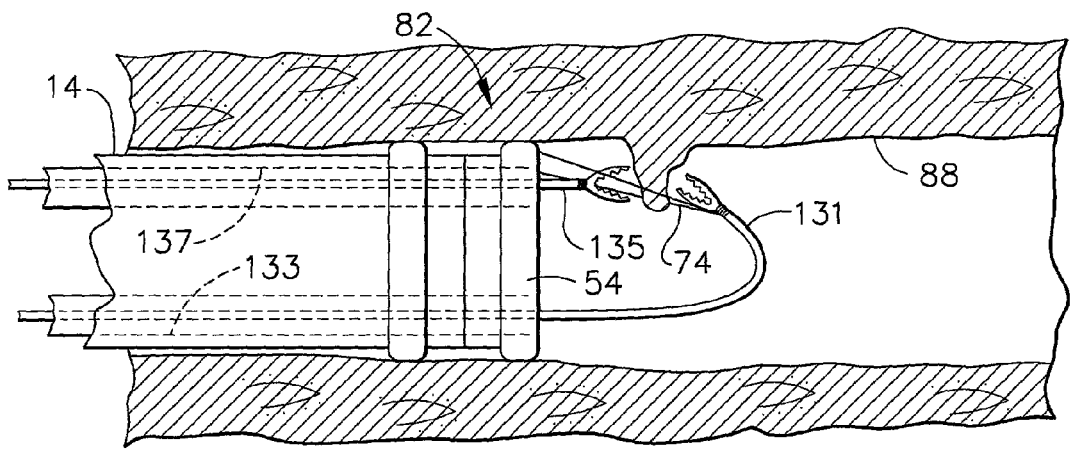
FIG. 23 is a side view showing an embodiment of an end cap attached to a grasper inserted through an instrument channel of an endoscope to cooperate with second grasper inserted through a second instrument channel of the endoscope.

FIG. 23 shows a first grasper 131 inserted through a first instrument channel 133 of a multi-channeled endoscope 141 having at least two instrument channels. First grasper 131 is connected to an embodiment of pivot arm 74. First grasper 131 can cooperate with a second grasper 135 inserted through a second instrument channel 137 to perform work on tissue distal to and on the periphery of multi-channeled endoscope 141.

Figure 24:
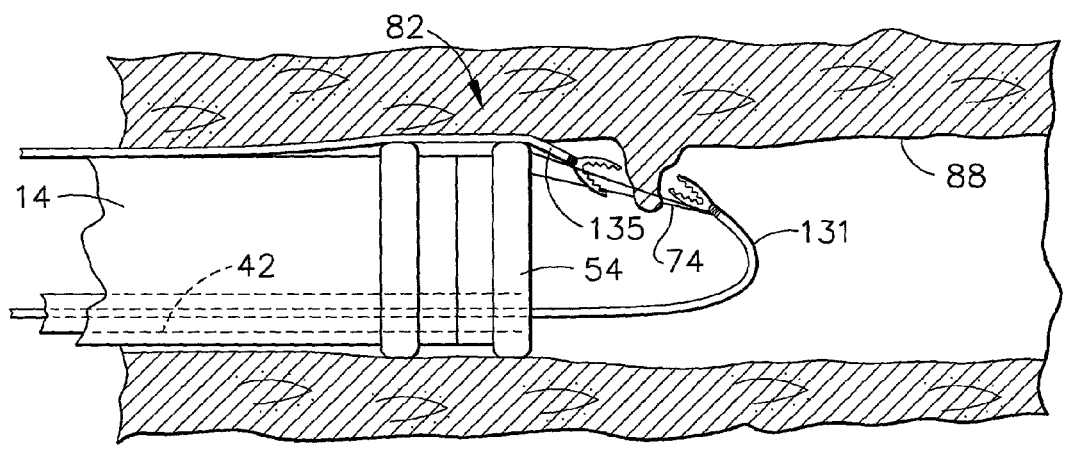
FIG. 24 is a side view showing an embodiment of an end cap attached to a grasper inserted through an instrument channel of an endoscope to cooperate with second grasper inserted alongside the endoscope.

FIG. 24 shows a first grasper 131 inserted through an instrument channel 42 of an endoscope 14. First grasper 131 is connected to an embodiment of pivot arm 74. First grasper 131 can cooperate with a second grasper 135 inserted alongside endoscope 14. Additional instruments may also be inserted to cooperate with first grasper 131.

The embodiments shown illustrate the use of the invention in connection with an endoscope within a body lumen. However, the invention is not limited to use within a naturally occuring body lumen, but is also useful in a variety of minimally invasive medical procedures, including without limitation medical procedures performed through laparoscopic incisions for access to body cavities and internal organs of the body. The invention also encompasses apparatus and methods employing endoscopic devices in general, including various forms and variations of endoscopes, including without limitation: laparascopes, gastroscopes, peritoneoscopes, sigmoidoscopes, fiberoptic endoscopes, and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An apparatus for use in a medical procedure, the apparatus comprising:

a first flexible medical instrument insertable within an instrument channel of an endoscope, the medical instrument having a first end-effector;

an arm adapted for connection to the distal end of an endoscope, the arm being adapted to guide the motion of the first end-effector, wherein the first end effector engages the arm about a first axis of rotation; and a second medical instrument having a second end-effector, wherein the second end effector engages the first end effector for rotation of the first end effector relative to the second end effector about a second axis of rotation, and wherein the first and second axis of rotation are substantially colinear.

* * * * *